United States Patent
Halpern et al.

(10) Patent No.: US 11,135,149 B2
(45) Date of Patent: Oct. 5, 2021

(54) SALT ACTIVATABLE WATER RESISTANT COSMETIC COMPOSITION

(71) Applicant: L'OREAL, Paris (FR)

(72) Inventors: Susan Halpern, Basking Ridge, NJ (US); Brian Bodnar, Manasquan, NJ (US); Nicholas David Stebbins, Clark, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/664,782

(22) Filed: Jul. 31, 2017

(65) Prior Publication Data

US 2019/0029942 A1    Jan. 31, 2019

(51) Int. Cl.
| | |
|---|---|
| *A61K 8/73* | (2006.01) |
| *A61K 8/40* | (2006.01) |
| *A61K 8/35* | (2006.01) |
| *A61K 8/37* | (2006.01) |
| *A61Q 17/04* | (2006.01) |

(52) U.S. Cl.
CPC ............... *A61K 8/733* (2013.01); *A61K 8/35* (2013.01); *A61K 8/37* (2013.01); *A61K 8/40* (2013.01); *A61K 8/731* (2013.01); *A61Q 17/04* (2013.01)

(58) Field of Classification Search
CPC . A61K 8/733; A61K 8/37; A61K 8/40; A61K 8/731; A61K 8/35; A61Q 17/04
See application file for complete search history.

(56) References Cited

U.S. PATENT DOCUMENTS

2004/0109831 A1* 6/2004 Dodwell .................. A61K 8/29
                                                      424/59
2016/0081891 A1* 3/2016 Nakano .................... A61Q 1/02
                                                      424/59

OTHER PUBLICATIONS

Hsiang-Fa Liang, et al. Novel Method Using a Temperature-Sensitive Polymer (Methylcellulose) to Thermally Gel Aqueous Alginate as a pH-Sensitive Hydrogel, Biomacromolecules 2004, 5, 1917-1925.

* cited by examiner

*Primary Examiner* — Robert A Wax
*Assistant Examiner* — Quanglong N Truong
(74) *Attorney, Agent, or Firm* — McNees Wallace & Nurick LLC

(57) ABSTRACT

A cosmetic composition and a method for forming a water resistant cosmetic composition are disclosed. The composition includes a salt activatable component combination having a holoside compound and an alginate compound. The composition also includes at least one cosmetic active agent. The composition has an increased salt water resistance when the salt activatable component combination is activated by a salt activator compared to a composition without said salt activatable component combination.

20 Claims, No Drawings

SALT ACTIVATABLE WATER RESISTANT COSMETIC COMPOSITION

FIELD OF THE INVENTION

The present invention relates to cosmetic compositions having a salt activatable component combination and at least one cosmetic active agent that has an increased water resistance when the salt activatable component combination is activated by a salt activator, such as salt water, pool water or sweat.

BACKGROUND OF THE INVENTION

It is well known that exposure to sunlight can pose numerous hazards to the skin. These damaging effects may result not only from sunbathing but also from the sunlight exposure associated with daily outdoor activities. The major short-term hazard of prolonged exposure to sunlight or UV radiation is erythema, i.e., sunburn. Over the long term, however, malignant changes in the skin surface often occur. Numerous epidemiologic studies demonstrate a strong relationship between sunlight exposure and human skin cancer. Another long-term hazard of ultraviolet radiation is premature aging of the skin. This condition is characterized by wrinkling and pigment changes of the skin, along with other physical changes, such as cracking, solar dermatoses, ecchymoses, and loss of elasticity.

As a result of the abovementioned hazards associated with sunlight or UV radiation exposure, the general public's interest in the sun protection product market has grown considerably. Today, there are not only sunscreen products for sunbathing but there are also a variety of personal care products containing sunscreens, particularly cosmetic type products which are worn daily. "Personal care products" refer to health and cosmetic beauty aid products generally recognized as being formulated for beautifying and grooming the skin and hair. For example, personal care products include sunscreen products (e.g., lotions, skin creams, etc.), cosmetics, toiletries, and over-the-counter pharmaceutical products intended for topical usage.

Cosmetic compositions for protection against UV radiation must fulfill a number of requirements to be effective. First, they must absorb the appropriate wavelengths of ultraviolet radiation to prevent sunburn and other forms of cellular damage and aging of the skin. Second, these compositions are most often used to counteract long exposure in sunlight, near water, or under conditions where perspiration is induced, therefore, compositions must be resistant to water and stable in ultraviolet (UV) light/radiation.

Many conventional sunscreen products and their ingredients are deficient due to their inability to provide efficacious protection against broad spectrum and because they are known to provide significant reduction in protection after being in use for an extended period, thus protection is reduced precisely when it is most needed to counteract long exposure to sunlight.

In addition, conventional sunscreen products tend not to improve lastingness of make-up during outdoor activities.

Thus, there is a need for cosmetic compositions suitable for providing protection against the harmful effects of UV radiation to the skin or a keratinous substrate that are highly water resistant, have excellent photostability (i.e. remain high SPF after exposure to sun and salt water after a period of time) and promote lastingness of make-up during outdoor activities.

BRIEF DESCRIPTION OF THE INVENTION

The compositions, according to the present disclosure, are useable for delivery of cosmetically active agents or as protection from ultraviolet (UV) radiation, preferably during high intensity beach, sport or outdoor activities. The compositions, when applied and activated by a salt activator, form films on a keratinous substrate that are highly water resistant, provide hours of effective UV radiation protection and remain high SPF when exposed to salt activators, such as salt water or sweat.

In an exemplary embodiment, a cosmetic composition is provided. The composition includes a salt activatable component combination having a holoside compound and an alginate compound. The composition also includes at least one cosmetic active agent. The composition has an increased salt water resistance when the salt activatable component combination is activated by a salt activator compared to a composition without said salt activatable component combination.

In another exemplary embodiment, a method of forming a water-resistant composition is disclosed. The method includes applying a composition to the keratinous substrate. The composition includes a salt activatable component combination. The salt activatable component combination includes a holoside compound, an alginate compound and at least one cosmetic active agent. The composition is exposed to a salt activator to activate the salt activatable component combination. The composition having the activated salt, activatable component combination has an increased salt water resistance compared to a composition without said salt activatable component combination.

Other features and advantages of the present invention will be apparent from the following more detailed description of the preferred embodiment which illustrates, by way of example, the principles of the invention.

DETAILED DESCRIPTION OF THE INVENTION

It has surprisingly been found that the compositions of the present invention, which comprise at least one cosmetic active agent and a salt activatable component combination comprising a holoside compound and an alginate compound, provide increased water resistance, excellent photostability (i.e., remains high SPF), and lastingness of make-up during outdoor activities and/or in salt water when the salt activatable component combination is activated by a salt activator, such as salt water.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

As used herein, the expression "at least one" means one or more and thus includes individual components as well as mixtures/combinations.

The term "keratinous substrate" refers to skin, nails and/or hair.

An "active agent" or "cosmetic active agent" refers to any substance or combination of substances that can produce an effect on/in the body.

The term "salt activator" refers to composition, such as an aqueous composition, having at least 25 ppm of divalent salt. Example of salt activators include, but are not limited to, sweat, sea water, pool water and/or tap water.

The term "non-salt water" refers to water having less than 25 ppm of divalent salt. Non-salt water includes fresh water, spring water, deionized water, distilled water, or any other water that has less than 25 ppm of divalent salt.

Embodiments of the present invention will primarily be described in connection with cosmetic compositions comprising a cosmetic active agent for application to the keratinous substrate, particularly the skin, however, the present invention is not limited to these specific uses, and can include various cosmetic agents in order to achieve specific cosmetic effects on the skin (i.e., a hydrating makeup primer for lastingness of makeup).

The embodiments of the present invention can comprise, consist of, or consist essentially of any of the required or optional ingredients and/or limitations described herein.

One embodiment, according to the present invention, contemplates a cosmetic composition comprising: (1) A salt activatable component combination comprising: a holoside compound and an alginate and (2) a cosmetic active agent, wherein the cosmetic composition has an increased water resistance when the salt activatable component combination is activated by salt activator compared to a composition without said salt activatable component combination.

Holoside Compounds

The composition, according to the present invention, includes a holoside compound. As utilized herein, "holoside compound" includes holoside compounds and derivatives thereof. Suitable holoside compounds or derivatives thereof are chosen from known polysaccharides, disaccharides, or a combination thereof. Particularly suitable holoside compounds include methylcellulose, hydroxypropylmethylcellulose (HPMC), hydroxypropylcellulose (HPC) cellulose gum (CG), carrageenan, xanthan gum, and/or a combination thereof.

The holoside compound present in the composition according to the present invention are present in an amount of at least 0.25% by weight, or at least about 0.3% by weight, or at least about 0.4% by weight, or at least about 0.5% by weight, or at least about 0.75% by weight, or at least about 1.0% by weight, or at least about 2.0% by weight, or at least about 2.5% by weight, from about 0.25% to 0.5% by weight, or from about 0.25% to 0.75% by weight, or from about 0.3% to 0.6% by weight, or from about 0.4% to 0.7% by weight, or from about 0.5% to 0.75% by weight, or from about 0.25% to 1.0% by weight, or from about 0.5% to 1.0% by weight, based on the total active weight of the composition, including increments and ranges thereof and therebetween.

Alginate Compound

The composition, according to the present invention, includes an alginate compound. As utilized herein, "alginate compound" includes alginate compounds and derivatives thereof. Suitable alginate compounds include any alginate compounds that, when in a composition with a holoside or holoside derivative, are salt activatable to form a water resistant composition. Examples of suitable alginate compounds include, but are not limited to, naturally occurring alginate compounds (naturally occurring alginates may, for example, be derived from seaweed). As used herein, the term "naturally occurring" with respect to the alginate compound, means that the alginate compound utilized is found in nature or is prepared synthetically, but chemically equivalent to an alginate compound found in nature. Other alginate compounds which may be utilized include those which are derivatives of naturally occurring alginates, for example, a propylene glycol alginate. Preferably, the alginate compound utilized herein is a naturally occurring alginate.

A particularly suitable alginate compound for use in the present compositions is sodium alginate. Sodium alginate is commercially available from a variety of sources including, for example, as SALTIALGINE GS 300, commercially available from SKW Bio-Systems, Boulogne, France. Other useful alginate compounds include SALTIALGINE S1100X, SALTIALGINE S 20, SALTIALGINE S 170, and SALTIALGINE S 300, all of which are also commercially available from SKW Bio-Systems. Additionally, NutraSweet Kelco Company supplies numerous alginate compounds including, for example, those in the KELGIN series, MANUCOL series, KELVIS series, KELCOSOL series, KELTONE series, MANUGEL series, KELMAR series, KELCOLOID series, KELSET series, LACTICOL series, ALGINADE series, DARILOID series, MARLOID series, and SHERBELIZER series and FMC BioPolymer, Philadelphia, USA supplies numerous alginate compounds in the PROTANAL series.

The alginate compound present in the composition according to the invention is present in an amount of at least 0.25% by weight, or at least about 0.3% by weight, or at least about 0.4% by weight, or at least about 0.5% by weight, or at least about 0.75% by weight, or at least about 1.0% by weight, or at least about 2.0% by weight, or at least about 2.5% by weight, from about 0.25% to 0.5% by weight, or from about 0.25% to 0.75% by weight, or from about 0.3% to 0.6% by weight, or from about 0.4% to 0.7% by weight, or from about 0.5% to 0.75% by weight, or from about 0.25% to 1.0% by weight, or from about 0.5% to 1.0% by weight, based on the total active weight of the composition, including increments and ranges thereof and therebetween.

Cosmetic Active Agent

The composition, according to the present invention, includes a cosmetic active agent. The cosmetic active agent may comprise any known suitable cosmetic active agent. For example, the cosmetic compositions, according to an embodiment of the present invention, may include one more of an active agent selected from but not limited to: UV filters (as more fully described below), active ingredients for artificially tanning and/or browning the skin (self-tanning agents) and more particularly dihydroxyacetone (DHA), anti-aging and/or anti-oxidation agents, free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in any one or more of suitable phases of the composition (i.e., aqueous and/or fatty (oil) phase.)

The cosmetic active agent will be present in amounts ranging from about 0.01% to 80%, in some embodiments from about 0.1% to 60%, and in some embodiments from about 0.5% to 50% by weight, all weights based on the total weight of the composition. Thus, in various embodiments, the active agent is present in a composition in a weight percent amount from 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, to about 80 percent by weight, including increments and ranges thereof and therebetween.

UV Filters

In one embodiment, the composition, according to the present invention, includes UV filters. Particularly suitable UV filters are selected from organic and inorganic filters, the UV protectant active selected from Mexoryl SX, Eusolex 232, Tinosorb S, Uvinul T150, Mexoryl XL, Avobenzone, Uvinul A, merocyanine B C3, liquid (Octocrylene, Parsol MCX, Homosalate, Néohéliopan AP, Neoheliopan OS, Tinosorb WPGL, Tinosorb A2B, nanoTiO$_2$ MT100TV, nanoTiO$_2$ MTAQ, hybridizer, Sunsil TIN50.

The UV filter will be present in amounts ranging from about 0.01% to 60%, in some embodiments from about 0.1% to 50%, and in some embodiments from about 0.5% to 40% by weight, all weights based on the total weight of the composition. Thus, in various embodiments, the UV filter is present in a composition in a weight percent amount from 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to about 60 percent by weight, including increments and ranges thereof and therebetween. According to some particularly suitable embodiments, compositions, according to the disclosure, may comprise the UV filter(s) in an amount of from 10 to 30% by weight, and in some embodiments from 15 to 25% by weight, and in some embodiments about 20% by weight in relation to the total weight of the composition.

In other examples, more generally, UV filter may be selected from any of a variety of UV filters. The UV filter can be selected from inorganic UV filters, organic UV filters, and mixtures thereof.

Inorganic UV Filter

The composition, according to the present invention, may comprise at least one inorganic UV filter. If two or more inorganic UV filters are used, they may be the same or different.

The inorganic UV filter used for the present invention may be active in the UV-A and/or UV-B region. The inorganic UV filter may be hydrophilic and/or lipophilic. The inorganic UV filter is, in some embodiments, insoluble in solvents, such as water, and ethanol commonly used in cosmetics.

It is in some embodiments desirable that the inorganic UV filter be in the form of a fine particle such that the mean (primary) particle diameter thereof ranges from 1 nm to 50 nm, and in some embodiments 5 nm to 40 nm, and in some embodiments 10 nm to 30 nm. The mean (primary) particle size or mean (primary) particle diameter herein is an arithmetic mean diameter.

The inorganic UV filter can be selected from the group consisting of silicon carbide, metal oxides, which may or may not be coated, and mixtures thereof. And in some embodiments, the inorganic UV filters are selected from pigments (mean size of the primary particles: generally from 5 nm to 50 nm, and in some embodiments from 10 nm to 50 nm) formed of metal oxides, such as, for example, pigments formed of titanium oxide (amorphous or crystalline in the rutile and/or anatase form), iron oxide, zinc oxide, zirconium oxide, or cerium oxide, which are all UV photoprotective agents that are well known per se. And in some embodiments, the inorganic UV filters are selected from titanium oxide, zinc oxide, and in some embodiments, titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes, such as beeswax, (meth)acrylic polymers, organic UV filters, and (per)fluoro compounds. It is in some embodiments desirable for the coating to include at least one organic UV filter. As the organic UV filter in the coating, a dibenzoylmethane derivative, such as butyl methoxydibenzoylmethane (Avobenzone) and 2,2'-Methylenebis[6-(2H-Benzotriazol-2-yl)-4-(1,1,3,3-Tetramethyl-Butyl)Phenol](Methylene Bis-Benzotriazolyl Tetramethylbutylphenol) marketed as "TINOSORB M" by BASF, may be desirable.

Of course, the inorganic UV filter made of metal oxides may, before their treatment with silicones, have been treated with other surfacing agents, in particular, with cerium oxide, alumina, silica, aluminum compounds, silicon compounds, or their mixtures. The coated inorganic UV filter may have been prepared by subjecting the inorganic UV filter to one or more surface treatments of a chemical, electronic, mechano-chemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filter may be titanium oxides coated: with silica, such as the product "Sun veil" from Ikeda, and "Sunsil TIN 50" from Sunjin Chemical; with silica and with iron oxide, such as the product "Sunveil F" from Ikeda; with silica and with alumina, such as the products "Microtitanium Dioxide MT 500 SA" from Tayca, "Tioveil" from Tioxide, and "Mirasun TiW 60" from Rhodia; with alumina, such as the products "Tipaque TTO-55 (B)" and "Tipaque TTO-55 (A)" from Ishihara, and "UVT 14/4" from Kemira; with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck; with alumina and with aluminum laurate, such as the product "Microtitanium Dioxide MT 100 S" from Tayca; with iron oxide and with iron stearate, such as the product "Microtitanium Dioxide MT 100 F" from Tayca; with zinc oxide and with zinc stearate, such as the product "BR351" from Tayca; with silica and with alumina and treated with a silicone, such as the products "Microtitanium Dioxide MT 600 SAS", "Microtitanium Dioxide MT 500 SAS", and "Microtitanium Dioxide MT 100 SAS" from Tayca; with silica, with alumina and with aluminum stearate and treated with a silicone, such as the product "STT-30-DS" from Titan Kogyo; with silica and treated with a silicone, such as the product "UV-Titan X 195" from Kemira; with alumina and treated with a silicone, such as the products "Tipaque TTO-55 (S)" from Ishihara or "UV Titan M 262" from Kemira; with triethanolamine, such as the product "STT-65-S" from Titan Kogyo; with stearic acid, such as the product "Tipaque TTO-55 (C)" from Ishihara; or with sodium hexametaphosphate, such as the product "Microtitanium Dioxide MT 150 W" from Tayca. Other titanium oxide pigments treated with a silicone are, and in some embodiments TiO$_2$ treated with octyltrimethylsilane and for which the mean size of the individual particles is from 25 and 40 nm, such as that marketed under the trademark "T 805" by Degussa Silices, TiO$_2$ treated with a polydimethylsiloxane and for which the mean size of the individual particles is 21 nm, such as that marketed under the trademark "70250 Cardre UF $TiO_2Si_3$" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

And in some embodiments, the following coated $TiO_2$ can be used as the coated inorganic UV filter: Stearic acid (and) Aluminum Hydroxide (and) $TiO_2$, such as the product "MT-100 TV" from Tayca, with a mean primary particle diameter of 15 nm; Dimethicone (and) Stearic Acid (and) Aluminum Hydroxide (and) $TiO_2$, such as the product "S A-TTO-S4" from Miyoshi Kasei, with a mean primary particle diameter of 15 nm; Silica (and) $TiO_2$, such as the product "MT-100 WP" from Tayca, with a mean primary particle diameter of 15 nm; Dimethicone (and) Silica (and) Aluminum Hydroxide (and) $TiO_2$, such as the product "MT-Y02" and "MT-Y-110 M3 S" from Tayca, with a mean primary particle diameter of 10 nm; Dimethicone (and) Aluminum Hydroxide (and) $TiO_2$, such as the product "SA-TTO-S3" from Miyoshi Kasei, with a mean primary particle diameter of 15 nm; Dimethicone (and) Alumina (and) $TiO_2$, such as the product "UV TITAN MI 70" from Sachtleben, with a mean primary particle diameter of 15 nm; and Silica (and) Aluminum Hydroxide (and) Alginic Acid (and) $TiO_2$, such as the product "MT-100 AQ" from Tayca, with a mean primary particle diameter of 15 nm. In terms of UV filtering ability, $TiO_2$ coated with at least one organic UV filter is more desirable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ". The uncoated zinc oxide pigments are, for example: those marketed under the trademark "Z-cote" by Sunsmart; those marketed under the trademark "Nanox" by Elementis; and those marketed under the trademark "Nanogard WCD 2025" by Nanophase Technologies. The coated zinc oxide pigments are, for example: those marketed under the trademark "Oxide Zinc CS-5" by Toshiba (ZnO coated with polymethylhydrosiloxane); those marketed under the trademark "Nanogard Zinc Oxide FN" by Nanophase Technologies (as a 40% dispersion in Finsolv TN, $C_{12}$-$C_{15}$ alkyl benzoate); those marketed under the trademark "Daitopersion Zn-30" and "Daitopersion Zn-50" by Daito (dispersions in oxyethylenated polydimethylsiloxane/ cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane); those marketed under the trademark "SPD-Z1" by Shin-Etsu (ZnO coated with a silicone-grafted acrylic polymer dispersed in cyclodimethylsiloxane); those marketed under the trademark "Escalol Z100" by ISP (alumina-treated ZnO dispersed in an ethylhexyl methoxycinnamate/PVP-hexadecene copolymer/methicone mixture); those marketed under the trademark "Fuji ZnO—SMS-10" by Fuji Pigment (ZnO coated with silica and polymethylsilsesquioxane); and those marketed under the trademark "Nanox Gel TN" by Elementis (ZnO dispersed at 55% in $C_{12}$-$C_{15}$ alkyl benzoate with hydroxystearic acid polycondensate). The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220". The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira. Coated inorganic UV filters are desirable, because the UV filtering effects of the inorganic UV filters can be enhanced. In addition, the coating(s) may help uniformly or homogeneously disperse the UV filters in the composition, according to the present invention.

Organic UV Filter

The compositions, according to the disclosure, may comprise at least one organic UV filter. If two or more organic UV filters are used, they may be the same or different. The organic UV filter used for the present invention may be active in the UV-A and/or UV-B region. The organic UV filter may be hydrophilic and/or lipophilic. The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from a-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof. Anthranilic compounds: Menthyl anthranilate, marketed under the trademark "Neo Heliopan MA" by Haarmann and Reimer. Dibenzoylmethane compounds: Butyl methoxydibenzoylmethane, marketed, in particular, under the trademark "Parsol 1789" by Hoffmann-La Roche; and isopropyl dibenzoylmethane. Cinnamic compounds: Ethylhexyl methoxycinnamate, marketed, in particular, under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate. Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer. Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex. Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxyb enzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethyl-amino-2-hydroxybenzoyl)benzoate (UVINUL A+ by BASF). β,β-Diphenylacrylate compounds: Octocrylene, marketed in particular under the trademark "Uvinul N539" by BASF; and Etocrylene, marketed in particular under the trademark "Uvinul N35" by BASF. Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVTNUL T150» by BASF. Benzotriazole compounds, in particular, phenylbenzotriazole derivatives: 2-(2H-b enzotriazole-2-yl)-6-dodecyl-4-methylpheno, branched and linear; and those described in U.S. Pat. No. 5,240,975. Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche. Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer. Imidazoline compounds: Ethylhexyl dimethoxybenzylidene dioxoimidazoline propionate. Bis-benzoazolyl compounds: The derivatives as described in EP-669,323 and U.S. Pat. No. 2,463,264. Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed, in particular, under the trademark "Escalol 507" by ISP, glyceryl PABA, and PEG-25 PABA, marketed under the trademark "Uvinul P25" by BASF. Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or- "Mexoryl XL" by L'Oreal. Benzoxazole compounds: 2,4-bis[5-1(dimethylpropyl)benzoxazol-2-yl-(4-phenyl)imino]-6-(2-ethylhexyl) imino-1,3,5-triazine, marketed under the trademark of Uvasorb K2A by Sigma 3V. Screening polymers and screening silicones: The silicones described in WO 93/04665. Dimers derived from a-alkylstyrene: The dimers described in DE-19855649. 4,4-Diarylbutadiene compounds: 1,1-dicarboxy(2,2'-dimethylpropyl)-4,4-diphenylbutadiene.

It is in some embodiments desirable that the organic UV filter(s) be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,r-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl) amino]-s-triazine, 2,4,6-tris-(di-phenyl)-triazine, 2,4,6-tris-(ter-phenyl)-triazine, methylene bis-benzotrizolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis [5-1 (dimethylpropyl)benzoxazol-2-yl-(4-phenyl)imino]-6-(2-ethylhexyl)imino-1,3,5-triazine, camphor benzylkonium methosulfate, and mixtures thereof.

Other Optional Ingredients

The compositions, according to the disclosure, may include one or more of a variety of optional ingredients, selected from but not limited to, one or more standard cosmetic adjuvants chosen from: oils, waxes, organic solvents, fillers, ionic or nonionic, hydrophilic or lipophilic thickeners, softeners, humectants, opacifiers, stabilizers, emollients, silicones, antifoams, fragrances, preserving agents, surfactants, active agents, coloring agents, cationic polymers, propellants, neutralizing or pH-adjusting agents (e.g., citric acid, triethylamine (TEA) and sodium hydroxide), conditioning or softening agents (e.g., panthenol and allantoinin), extracts, such as botanical extracts, free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase) or any other ingredient usually used in cosmetics and/or dermatology.

Optional ingredients may be present in the compositions in amounts generally ranging from about 0.01% to 25%, in some embodiments from about 0.1% to 20%, and in some embodiments from about 0.5% to 15% by weight, all weights based on the total weight of the composition. Thus, in various embodiments, an SPF booster may be present in a composition in a weight percent amount from 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to 25.0 percent by weight, including increments and ranges thereof and therebetween.

Those skilled in the art will take care to select the optional additional compound(s) mentioned above and/or the amounts thereof such that the advantageous properties intrinsically associated with the compositions, in accordance with the invention, are not, or are not substantially, adversely affected by the envisaged addition(s). Those skilled in the art will choose said active agent(s) according to the desired effect on the skin, hair, eyelashes, eyebrows, or nails.

In some embodiments of the invention, the inventive compositions are devoid or substantially devoid of synthetic film formers. These compositions have better aesthetics and feel more natural while still being efficacious.

In some embodiments of the invention, the compositions disclosed herein are applied to a keratinous substrate to protect it from UV radiation.

Salt Activator

The composition, according to the present disclosure, is activated by a salt activator. The salt activator is a salt-containing composition, such as an aqueous solution or dispersion, having at least 25 ppm of divalent salt. Examples of salt activators include, but are not limited to, sweat, sea water and/or pool water. The divalent salt present in the salt activator includes, but is not limited to, calcium and/or magnesium salts. The salt activator preferably contacts the composition after application to the keratinous substrate. The salt activator is provided in an external environment, such as, the beach or at a pool, wherein the person who has applied the composition exposes the composition to the salt activator. While not wishing to be bound by theory or explanation, it is believed that the exposure to the salt activator to the already applied composition forms a gel network that provides a superior water resistance, particularly to salt water, because the gel network is able to form preferentially along the keratinous substrate in the locations where the composition is applied with minimal exposure to shear or other forces that damage the gel network. Particularly, according to an embodiment of the invention, the un-activated salt activatable component combination must be in contact with the keratinous substrate (e.g., skin) prior to activation or undesirable gelation or gel bodies would result in the formulation, preventing the water resistant film from being effectively formed when applied.

Water Resistance

Water resistance, as utilized herein includes a measure of stability of a compositional property when exposed to water. In one embodiment, water resistance includes the stability of an SPF of a UV Filter containing composition. To calculate the stability of SPF, a procedure is performed measuring the SPF of a dried composition at an initial time ($SPF_i$) and immersing the dried composition in water for a set period of time. In one embodiment, the time of immersion is 20 minutes. After immersion, the composition is dried and the SPF is measured ($SPF_f$). The water resistance (WR) is calculated using the following formula:

$$WR = \frac{SPF_f}{SPF_i} \times 100 :$$

$SPF_i$=SPF initial $SPF_f$=SPF post 20 minute immersion.

The composition according to certain embodiments of the present invention include a water resistance of greater than 70%, or greater than 75%, or greater than 80%, or greater than 85%, or greater than 90%, or greater than 92%, or greater than 94%, or greater than 96%.

Method

In order to form compositions according to the present invention, a water phase is prepared with water, and, according to some embodiments, water, alginate, holoside and hydrosoluble emulsifiers and UV filters. The water phase components are combined under agitation to provide the solubilization of hydrosoluble materials. The method further includes preparing an oil phase with an active, in some such embodiments including, at least one UV filter, and in some embodiments fatty oils that are heat soluble, as solvents and fat-soluble emulsifiers. The oil phase components are agitated to provide a translucent bulk. The water phase and oil phase were combined and agitated sufficiently to form a visually stable composition. Other ingredients are added in their respective phase components and can optionally be provided as additional phases or separately added to the composition.

Alternatively, in another embodiment, the water phase may be prepared with water, and, according to some embodiments, water, alginate, and hydrosoluble emulsifiers and UV filters. The water phase is prepared under agitation. An oil phase is prepared with an active, for example, a UV filter, and in some embodiments fatty oils that are heat soluble, as solvents and fat-soluble emulsifiers. The oil phase components are combined with agitation to provide a translucent bulk. The water phase and oil phase were combined and agitated sufficiently to form an emulsion. The holoside is then added to the emulsion and homogenized to form a visually stable composition.

One embodiment, according to the present invention, includes a method of protecting a keratinous substrate from UV radiation. The method includes applying a composition including an alginate and holoside, according to the present invention, to a keratinous substrate, such as skin. Applying may include application of the composition and manual rubbing or otherwise distributing the composition onto the keratinous substrate.

The method further includes exposing the applied composition to a salt activator. The exposing may include contacting the composition with salt water, for example in the ocean. Alternatively, exposing may include contacting the composition with pool water or other salt activator having at least 25 ppm of divalent salt. In another embodiment, exposing includes contact with sweat (or sweating) with the composition applied. After activating the composition with exposure to the salt activator, the composition has greater water resistance, particularly with respect to salt water, than a composition that has not been exposed to a salt activator or a composition that has had a salt added directly to the composition prior to application.

The following examples serve to illustrate the invention without however exhibiting a limiting character. In these examples, the amounts of the composition ingredients are given as weight percentages relative to the total weight of the composition.

EXAMPLES

In order to form the compositions, according to the examples and comparative examples, the following process was utilized. The water phase is prepared with water, and, according to some embodiments, water, alginate, holoside and hydrosoluble emulsifiers and UV filters. In the composition presented in the examples, all the material of water phase is weighted in a beaker. The water phase is prepared at room temperature, under mechanical agitation to provide the solubilization of hydrosoluble materials. The oil phase is prepared with an active, in some such embodiments including, at least one UV filter, and in some embodiments fatty oils that are heat soluble, as solvents and fat-soluble emulsifiers. The oil phase components, in a representative embodiment including UV filters from oil phase, fat-soluble, and heat soluble materials, are weighed in a beaker and heated to melting to 75° C., with mechanical agitation to provide a translucent bulk. The water phase and oil phase were combined and agitated sufficiently to form a visually stable composition.

In order to determine water resistance, the following procedure was performed. A sample containing 35-55 mg of a composition disclosed herein is applied to an Europlast PMMA plate and spread until an even film is formed. The film is then allowed to dry and settle for 15 minutes at room temperature. After the film is dried and settled on the plate, the initial SPF of the film is measured using LabSphere (take 5 measurements per plate). Next, using the Agilent Dissolution Apparatus, the plate with the film is fully immersed for 20 minutes in a water bath set to 25 degrees Celsius. After the 20 minutes of immersion, the plate is removed and allowed to dry at room temperature for 30 minutes. The SPF of the film on the plate is measured again (take 5 measurement per plate). The water resistance (WR) is calculated using the following formula:

$$WR = \frac{SPF_f}{SPF_i} \times 100:$$

$SPF_i$=SPF initial $SPF_f$=SPF post 20 minute immersion.

TABLE 1 shows water resistance values for an exemplary composition (Ex. 1) as well as comparative Examples (Comp. Ex. 1-3). Ex. 1 includes both the alginate and holoside (xanthan gum), wherein the comparative examples include examples with alginate only (Comp. Ex. 1), holoside only (Comp. Ex. 2) and a thickening polymer, sepigel, only (Comp. Ex. 3).

TABLE 1

| Phase | Chemical Name | Example 1 (wt %) | Comp. Ex. 1 (wt %) | Comp. Ex. 2 (wt %) | Comp. Ex. 3 (wt %) |
|---|---|---|---|---|---|
| A | Water | qs | qs | qs | qs |
|   | Alginate | 0.5 | 1 | 0 | 0 |
|   | Preservative | 0.7 | 0.7 | 0.7 | 0.7 |
| B | UV Filters | 20.01 | 20.01 | 20.01 | 20.01 |
|   | Emulsifier | 3 | 3 | 3 | 3 |
| C | Xanthan Gum | 0.5 | 0 | 1 | 0 |
|   | Sepigel | 0 | 0 | 0 | 1 |
|   | WATER RESISTANCE | 79% | 55% | 53% | 42% |

TABLES 2 and 3 show water resistance values for an exemplary composition (Ex. 2) as well as comparative Example (Comp. Ex. 4), and comparative example (Comp. Ex.4) or Example 2 combined with a well-known water resistant polymer (i.e., a commercially available colloidal system of a high molecular weight polyurethane polymer). Ex. 2 includes both the alginate and holoside (methylcellulose), wherein the comparative example includes examples with alginate only (Comp. Ex. 4).

TABLE 2

| Phase | Chemical Name | Example 2 (wt %) | Comp. Ex. 4 (wt %) |
|---|---|---|---|
| A | Water | qs | qs |
|   | Alginate | 0.5 | 1 |
|   | Preservative | 0.7 | 0.7 |
|   | Methylcellulose | 2.0 | 0 |
| B | UV Filters | 20.01 | 20.01 |
|   | Emulsifier | 3 | 3 |
|   | Xanthan Gum | 0.5 | 0 |
|   | Alcohol | 2.0 | 2.0 |

TABLE 3

| | Water Resistance | | |
|---|---|---|---|
| SPF VALUES | Prior to exposure | After Exposure | % Water Resistance |
| Comp. Ex. 4 | 26 | 17 | 65% |
| WR Polymer Baycusan C1004) + Comp. Ex. 4 | 51 | 42 | 82% |
| Activated with Salt Activator (Example 2) | 35 | 33 | 94% |
| Activated with Salt Activator (Example 2) + WR Polymer (Baycusan) | 53 | 46 | 87% |

TABLE 4 shows water resistance values for exemplary compositions (Ex. 3-6) having various holoside derivatives.

TABLE 4

| Phase | Chemical Name | Example 3 | Example 4 | Example 5 | Example 6 |
|---|---|---|---|---|---|
| A | Water | qs | qs | qs | qs |
|   | Alginate | 0.5 | 1 | 0 | 0 |
|   | Preservative | 0.7 | 0.7 | 0.7 | 0.7 |
| B | UV Filters | 20.01 | 20.01 | 20.01 | 20.01 |
|   | Emulsifier | 3 | 3 | 3 | 3 |
| C | HPMC | 0.5 | 0 | 1 | 0 |
|   | HPC | 0 | 0.5 | 0 | 0 |
|   | CG | 0 | 0 | 0.5 | 0 |
|   | Carageenan | 0 | 0 | 0 | 0.5 |
|   | WATER RESISTANCE | 91% | 71% | 80% | 77% |

TABLE 5 shows water resistance values for comparative compositions (Comp. Ex. 3-6) having salt added directly to formulation prior to application to a keratinous substrate. The comparative examples shown in TABLE 5 resulted in polymer networks that were destroyed by exposure to high shear, significantly reducing the water resistance. In addition, when the compositions having the directly added salt were stirred slowly, an agglomeration of gel formed in the composition forming an aesthetically undesirable composition (i.e., an insoluble, cross-linked gel would result, forming an undesirable formula). Furthermore, when the salt is directly added to the formulation prior to application to a keratinous substrate, the salt causes separation which leads to a formula/product that is not a cream or lotion form.

TABLE 5

| Phase | Chemical Name | Comp. Ex. 5 (wt %) | Comp. Ex. 6 (wt %) | Comp. Ex. 7 (wt %) | Comp. Ex. 8 (wt %) |
|---|---|---|---|---|---|
| A | Water | qs | qs | qs | qs |
| | Alginate | 0.5 | 0.5 | 0.5 | 0.5 |
| | Preservative | 0.7 | 0.7 | 0.7 | 0.7 |
| | HPMC | 0.5 | 0.5 | 0.5 | 0.5 |
| | Ca salt | 10 | 0.05 | 0 | 0 |
| | Mg salt | 0 | 0 | 0.3 | 0.005 |
| B | UV Filters | 20.01 | 20.01 | 20.01 | 20.01 |
| | Emulsifier | 3 | 3 | 3 | 3 |
| | Xanthan Gum | 0.5 | 0.5 | 0.5 | 0.5 |
| | Alcohol | 2 | 2 | 2 | 2 |
| WATER RESISTANCE | | 6% | 72% | 75% | 72% |

TABLE 6 shows the water resistance for exemplary compositions (Examples 7-14) exposed to various concentrations of calcium salt. As shown below Ex. 7-11 correspond to salt concentrations in ocean water, pool water and sweat.

TABLE 6

| Example | Alginate Amt (%) | Cellulose Type | Cellulose Amt (%) | Salt type, amt | Initial SPF (in vitro) | Final SPF (in vitro) | WR (in vitro) |
|---|---|---|---|---|---|---|---|
| 7 | 0.5 | HPMC | 0.5 | 6% Ca* | 32 | 29 | 91% |
| 8 | 0.5 | HPMC | 0.5 | 5% Ca* | 24 | 19 | 79% |
| 9 | 0.5 | HPMC | 0.5 | 1.5% Ca** | 29 | 25 | 86% |
| 10 | 0.5 | HPMC | 0.5 | 0.6% Ca** | 34 | 23 | 68% |
| 11 | 0.5 | HPMC | 0.5 | 0.1% Ca*** | 34 | 21 | 62% |
| 12 | 0.5 | HPMC | 0.5 | 0.08% Ca | 36 | 19 | 53% |
| 13 | 0.5 | HPMC | 0.5 | .06% Ca | 29 | 15 | 52% |
| 14 | 0.5 | HPMC | 0.5 | 0% Ca | 28 | 3 | 11% |

Ca+ percentages of calcium refer to the calcium source, which is $CaCl_2 \cdot 2H_2O$ (calcium chloride dihydrate)
*salt concentration corresponds to ocean water
**salt concentration corresponds to pool water
***salt concentration corresponds to sweat While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:
1. A cosmetic composition comprising:
a) a salt activatable component combination comprising:
about 0.4% to about 0.6% of a holoside compound by weight of the composition, the holoside being selected from the group consisting of methylcellulose, hydroxypropylmethylcellulose (HPMC), hydroxypropylcellulose (HPC) cellulose gum (CG), carrageenan, xanthan gum, and combinations thereof; and
about 0.4% to about 0.6% of an alginate compound by weight of the composition; and
b) at least one cosmetic active agent comprising at least one UV filter;
wherein the composition is devoid of synthetic film formers,
wherein the holoside compound and the alginate compound constitute a water resistant film precursor, and
wherein exposure of the cosmetic composition to a salt activator activates the salt activatable component combination such that the water resistant film precursor converts to a water resistant film and increases a water resistance of the composition.
2. The composition according to claim 1, wherein the holoside compound comprises.
3. The composition according to claim 1, wherein the holoside compound comprises hydroxypropylmethylcellulose (HPMC).
4. The composition according to claim 1, wherein the holoside and the alginate are each present in the composition in an amount of about 0.5% by weight of the composition.
5. The composition according to claim 1, wherein the alginate compound comprises a naturally occurring alginate.
6. The composition according to claim 1, wherein the alginate compound comprises sodium alginate.
7. The composition according to claim 1, wherein the at least one cosmetic agent includes a mixture of UV filters selected from the group consisting of butyloctyl salicylate, butyl methoxydibenzoylmethane, octocrylene, ethylhexyl salicylate, homosalate and combinations thereof.
8. The composition according to claim 7, wherein the UV filter includes each of butyloctyl salicylate, butyl methoxydibenzoylmethane, octocrylene, ethylhexyl salicylate, and homosalate.
9. The composition according to claim 1, wherein the salt activator is selected from the group consisting of sweat, sea water, pool water and combinations thereof.
10. A method of forming a water resistant composition comprising:
a) applying a composition to a keratinous substrate, the composition comprising:
i) a salt activatable component combination comprising:
about 0.4% to about 0.6% of a holoside compound by weight of the composition, the holoside being selected from the group consisting of methylcellulose, hydroxypropylmethylcellulose (HPMC), hydroxypropylcellulose (HPC) cellulose gum (CG), carrageenan, xanthan gum, and combinations thereof;
about 0.4% to about 0.6% of an alginate compound by weight of the composition; and
at least one cosmetic active agent comprising at least one UV filter,
wherein the holoside compound and the alginate compound constitute a water resistant film precursor, and wherein the composition is devoid of synthetic film formers; and then b) exposing the composition to a salt activator to activate the salt activatable component combination and to form a water resistant film from the water resistant film precursor on the keratinous substrate.

11. The method according to claim 10, wherein only upon exposure to water and a salt activator, the composition exhibits a water resistance that includes stability of the composition's initial SPF of at least 70%, and wherein the salt activator is an aqueous composition having a divalent salt, and is selected from the group consisting of sweat, sea water, pool water, and combinations thereof.

12. The method according to claim 10, wherein the holoside compound includes xanthan gum.

13. The method according to claim 10, wherein the alginate compound comprises sodium alginate, and wherein the composition further comprises each of hydrosoluble and fat-soluble emulsifiers.

14. The method according to claim 10, wherein the at least one cosmetic agent includes a mixture of UV filters.

15. The composition according to claim 1, further comprising each of hydrosoluble and fat-soluble emulsifiers.

16. An emulsified sunscreen composition, comprising:
a water phase comprising water, and a combination of at least one of each of:
about 0.4% to about 0.6% of alginates by weight of the composition;
about 0.4% to about 0.6% of holosides alginates by weight of the composition, the holosides being selected from the group consisting of methylcellulose, hydroxypropylmethylcellulose (HPMC), hydroxypropylcellulose (HPC) cellulose gum (CG), carrageenan, xanthan gum, and combinations thereof; and
hydrosoluble emulsifiers; and
an oil phase comprising at least one cosmetic active comprising one or a combination of UV filters, fatty oils that are heat soluble, and fat-soluble emulsifiers,
wherein the composition is devoid of synthetic film formers and divalent salts, and
wherein the composition has an initial SPF and when applied on a keratinous substrate followed by exposure to an aqueous salt activator, the alginates and the holosides react with the aqueous salt activator to form a water resistant such that the composition following formation of the water resistant film exhibits a water resistance that includes stability of the composition's initial SPF of at least 70%.

17. The cosmetic composition according to claim 1,
wherein the composition, when applied to a keratinous substrate, forms a water resistant film on the keratinous substrate only upon exposure to a salt activator comprising a water and a divalent salt.

18. The cosmetic composition according to claim 17, wherein upon exposure to water and the salt activator, the composition exhibits a water resistance that includes stability of the composition's initial SPF of at least 70%.

19. The cosmetic composition according to claim 17, wherein the salt activatable component combination comprises:
at least one of hydroxypropylmethylcellulose (HPMC), carrageenan, and xanthan gum; and
sodium alginate;
wherein the divalent salt is present at a concentration from about 0.6% to about 6% by weight of the salt activator.

20. The cosmetic composition according to claim 1, wherein the cosmetic composition is free of multivalent salts.

* * * * *